United States Patent
Kim et al.

(10) Patent No.: US 10,219,749 B2
(45) Date of Patent: Mar. 5, 2019

(54) SMART BED AND USER STATE MONITORING SYSTEM AND USER STATE MONITORING METHOD USING THE SAME

(71) Applicant: KOREA ELECTRONICS TECHNOLOGY INSTITUTE, Seongnam-si, Gyeonggi-do (KR)

(72) Inventors: Kunnyun Kim, Yongin-si (KR); Kwang Bum Park, Yongin-si (KR); Won Hyo Kim, Yongin-si (KR); Yeon Hwa Kwak, Seoul (KR)

(73) Assignee: KOREA ELECTRONICS TECHNOLOGY INSTITUTE, Seongnam-si (KR)

(*) Notice: Subject to any disclaimer, the term of this patent is extended or adjusted under 35 U.S.C. 154(b) by 0 days.

(21) Appl. No.: 15/891,282

(22) Filed: Feb. 7, 2018

(65) Prior Publication Data
US 2018/0160979 A1    Jun. 14, 2018

Related U.S. Application Data

(63) Continuation of application No. PCT/KR2016/001248, filed on Feb. 4, 2016.

(30) Foreign Application Priority Data

Aug. 7, 2015    (KR) .................. 10-2015-0111693

(51) Int. Cl.
*A61B 5/00* (2006.01)
*G01L 1/22* (2006.01)
(Continued)

(52) U.S. Cl.
CPC ............ *A61B 5/6892* (2013.01); *A47C 31/00* (2013.01); *A61B 5/113* (2013.01); *A61B 5/4809* (2013.01);
(Continued)

(58) Field of Classification Search
CPC ....... A61B 5/0816; A61B 5/4812; A61B 5/11; A61B 2562/0261; A61B 5/4815;
(Continued)

(56) References Cited

U.S. PATENT DOCUMENTS 5,964,720 A * 10/1999 Pelz .................... A61B 5/0002
                                                              600/483
6,468,234 B1 * 10/2002 Van der Loos .......... A61B 5/01
                                                              128/920
(Continued)

FOREIGN PATENT DOCUMENTS

EP          0347897 A1    12/1989
KR    10-2007-0006409 A    1/2007
(Continued)

OTHER PUBLICATIONS

International Search Report dated Jun. 7, 2016 of PCT/KR2016/001248 which is the parent application and its English translation—5 pages.
(Continued)

*Primary Examiner* — May Abouelela
(74) *Attorney, Agent, or Firm* — Knobbe Martens Olson & Bear LLP

(57) ABSTRACT

Provided is a smart bed for monitoring a state of a user. The smart bed includes a mattress including at least one flexible tactile sensor configured to sense a state of a user lying on the bed and a bed frame configured to support the mattress. The flexible tactile sensor is positioned below a specific portion of the user.

7 Claims, 13 Drawing Sheets

(51) Int. Cl.
| | |
|---|---|
| *G01L 1/18* | (2006.01) |
| *A47C 31/00* | (2006.01) |
| *A61B 5/113* | (2006.01) |
| *G01L 5/00* | (2006.01) |
| *G08B 21/02* | (2006.01) |
| *G08B 21/04* | (2006.01) |
| *G01L 1/20* | (2006.01) |
| *A61G 7/05* | (2006.01) |
| *A61B 5/08* | (2006.01) |
| *A47C 23/00* | (2006.01) |
| *A61B 5/11* | (2006.01) |

(52) U.S. Cl.
CPC .......... *A61B 5/4818* (2013.01); *A61B 5/4836* (2013.01); *G01L 1/205* (2013.01); *G01L 1/22* (2013.01); *G01L 1/2287* (2013.01); *G01L 5/00* (2013.01); *G08B 21/02* (2013.01); *G08B 21/04* (2013.01); *A47C 23/00* (2013.01); *A61B 5/0002* (2013.01); *A61B 5/08* (2013.01); *A61B 5/1102* (2013.01); *A61B 2562/0261* (2013.01); *A61B 2562/04* (2013.01); *A61B 2562/164* (2013.01); *A61B 2562/225* (2013.01); *A61G 7/05* (2013.01); *A61G 2203/32* (2013.01); *A61G 2203/34* (2013.01); *G08B 21/0415* (2013.01); *G08B 21/0461* (2013.01)

(58) Field of Classification Search
CPC ..... A61B 5/4818; A61B 5/6892; A61B 5/113; A61B 5/746; A61B 5/4806; A61B 5/1115; G01L 19/08; G01L 1/205; G01L 1/22; G01L 1/2287; G01L 5/00
USPC ................ 600/300, 587, 595; 340/573.1
See application file for complete search history.

(56) References Cited

U.S. PATENT DOCUMENTS

| | | | | |
|---|---|---|---|---|
| 7,431,700 | B2 * | 10/2008 | Aoki | A61B 5/1135 |
| | | | | 600/529 |
| 2003/0016209 | A1 | 1/2003 | Narusawa et al. | |
| 2004/0155870 | A1 | 8/2004 | Middleton | |
| 2005/0113711 | A1 * | 5/2005 | Nakatani | A61B 5/103 |
| | | | | 600/534 |
| 2005/0124864 | A1 * | 6/2005 | Mack | A61B 5/024 |
| | | | | 600/300 |
| 2006/0176280 | A1 | 8/2006 | Griffin | |
| 2006/0246242 | A1 * | 11/2006 | Siegel | A23B 4/10 |
| | | | | 428/34.1 |
| 2007/0195062 | A1 | 8/2007 | Guthrie | |
| 2008/0097250 | A1 * | 4/2008 | Tochigi | A61B 5/024 |
| | | | | 600/595 |
| 2008/0228097 | A1 * | 9/2008 | Tang | A61B 5/113 |
| | | | | 600/536 |
| 2008/0275314 | A1 * | 11/2008 | Mack | A61B 5/024 |
| | | | | 600/301 |
| 2010/0094139 | A1 * | 4/2010 | Brauers | A61B 5/024 |
| | | | | 600/484 |
| 2011/0295083 | A1 * | 12/2011 | Doelling | A61B 5/103 |
| | | | | 600/301 |
| 2012/0259248 | A1 * | 10/2012 | Receveur | G16H 50/30 |
| | | | | 600/595 |
| 2013/0072767 | A1 * | 3/2013 | Imamura | A61B 5/024 |
| | | | | 600/301 |
| 2013/0137998 | A1 * | 5/2013 | Lange | A61B 5/113 |
| | | | | 600/483 |
| 2013/0144178 | A1 * | 6/2013 | Halperin | A61B 5/113 |
| | | | | 600/508 |
| 2014/0046184 | A1 * | 2/2014 | Heinrich | A61B 5/0064 |
| | | | | 600/438 |
| 2014/0371635 | A1 * | 12/2014 | Shinar | A61B 5/6891 |
| | | | | 600/595 |
| 2015/0164409 | A1 * | 6/2015 | Benson | G16H 50/30 |
| | | | | 600/301 |
| 2015/0282304 | A1 * | 10/2015 | Ely | H05K 1/0281 |
| | | | | 361/750 |
| 2015/0327792 | A1 * | 11/2015 | Shinar | A61B 5/6892 |
| | | | | 600/529 |
| 2016/0022218 | A1 * | 1/2016 | Hayes | A61G 7/005 |
| | | | | 600/301 |
| 2016/0174892 | A1 * | 6/2016 | Benson | G16H 50/30 |
| | | | | 600/301 |
| 2016/0178462 | A1 * | 6/2016 | Gacoin | G01B 7/18 |
| | | | | 428/328 |
| 2017/0079144 | A1 * | 3/2017 | Coleman | H05K 1/0283 |

FOREIGN PATENT DOCUMENTS

| | | |
|---|---|---|
| KR | 10-2008-0096621 A | 10/2008 |
| KR | 10-2009-0047674 A | 5/2009 |
| KR | 20-2009-0009178 U | 9/2009 |
| KR | 10-1057001 B1 | 8/2011 |
| KR | 10-2013-0141289 A | 12/2013 |
| KR | 10-2014-0001612 A | 1/2014 |
| WO | 2012072240 A1 | 6/2012 |

OTHER PUBLICATIONS

Office Action of corresponding Korean Patent Application No. 10-2015-0111693—5 pages (dated Jun. 28, 2016).

* cited by examiner

SMART BED AND USER STATE MONITORING SYSTEM AND USER STATE MONITORING METHOD USING THE SAME

CROSS-REFERENCE TO RELATED APPLICATIONS

This application is a continuation application, and claims the benefit under 35 U.S.C. §§ 120 and 365 of PCT Application No. PCT/KR2016/001248, filed on Feb. 4, 2016, which is hereby incorporated by reference. PCT/KR2016/001248 also claimed priority from Korean Patent Application No. 10-2015-0111693 filed on Aug. 7, 2015, which is hereby incorporated by reference.

BACKGROUND

Field

The present disclosure relates to a smart bed, and a user state monitoring system and a user state monitoring method using the same, and more particularly, to a smart bed that can accurately detect a state of a user and monitor the state of the user by using a flexible tactile sensor, and a user state monitoring system and a user state monitoring method using the same.

Related Art

There are apparatuses for measuring electrocardiogram, body temperature, blood pressure, pulse rate and blood glucose level, which are devices for measuring bio-signals and the apparatuses check a health state of a user or a patient or detect or measure the bio-signals and display the detected or measured bio-signals on a screen in order to treat the user or patient.

However, since the bio-signal measuring apparatus needs to include a precise sensor for measuring the bio-signal of the user and needs to calculate the measured bio-signal and to calculate a statistic value, the bio-signal measuring apparatus is expensive.

In addition, a warble measuring apparatus such as a garment or a wrist watch or a belt may cause discomfort and inconvenience to the user or the patient, and there are many complicated apparatuses for the user or patient to use.

Korean Patent Unexamined Publication No. 10-2013-0141289 relates to a system and a method for monitoring a bio-signal for inducing a deep sleep and provides a system for monitoring a bio-signal, which includes a bio-signal measuring unit including a fiber based sensor and measuring the bio-signal of a user who is in his/her sleep by means of the sensor, a sleep state detecting unit detecting analyzing the bio-signal and detecting the sleep state of the user, and a health management service providing unit providing a sleep pattern of the user acquired by collecting and analyzing the sleep state of the user to a health management service with to a terminal possessed by the user during a predetermined period.

Korean Patent Registration No. 10-1057001 relates to a system for dealing with a sleeping disorder through real-time monitoring and provides a system which is configured to include a respiratory sensing unit for transmitting a result of sensing a gas breathing to a respiratory apparatus by being worn on the respiratory apparatus of a human body, a human body operation sensing unit worn on the human body and transmitting a result of sensing a motion and a posture of the human body, a human body information processing unit generating a control signal for controlling a sleeping state of the human body according to the result sensed by the human body operation sensing unit, and a sleep state control unit executing an operation for controlling the sleeping state of the human body according to the control signal from the human body information processing unit to induce a sleeping posture of a sleeper to be changed, deal with the sleeping order such as apnea, or the like, and enable the sleeper to take a deep sleep.

The present disclosure is made in association with a Korean national research and development project (research project name: Development of a motion game and bracelet type wearable device recognizing hand gesture with offering SDK for AR/VR, project identification number: 2017-0-00595).

The disclosure of this section is to provide background of the described technology. Applicant notes that this section may contain information available before this application. However, by providing this section, Applicant does not admit that any information contained in this section constitutes prior art.

SUMMARY

An aspect of the present invention provides a smart bed that can sense a state of a user through a double-sided flexible tactile sensor.

An aspect of the present invention also provides a smart bed that can sense the state of the user just in a state in which the user lies in a bed without the need of using a separate apparatus or performing a separate pre-procedure.

An aspect of the present invention also provides a user state monitoring system and a user state monitoring method that can monitor the state of the user such as breathing, heartbeat, whether the user moves, or the like without giving a sense of discomfort to the user.

Another aspect of the present invention provides a smart bed which includes: a mattress including at least one flexible tactile sensor sensing a state of a user who lies; and a bed frame loading the mattress, in which the at least one flexible tactile sensor is positioned at a point corresponding to a specific portion of the user who lies on the mattress.

In an embodiment, the flexible tactile sensor may be embedded in a mattress body.

In an embodiment, the flexible tactile sensor may include a detachment/attachment portion on one surface and may be detached from/attached to the mattress body through the detachment/attachment portion.

In an embodiment, the flexible tactile sensor may be positioned at a point corresponding to a chest of the user who lies on the mattress body and positioned across the chest of the user.

In an embodiment, the flexible tactile sensor may be positioned across a heart of the user.

In an embodiment, the flexible tactile sensor may be positioned at a point corresponding to an abdomen of the user who lies on the mattress body and positioned across the abdomen of the user.

In an embodiment, the flexible tactile sensor may include a tactile sensor array constituted by a plurality of tactile sensor modules.

In an embodiment, the tactile sensor module may include a polymer layer, a first metal layer formed on the top of the polymer layer, a first sensor layer including a strain gauge formed on the top of the first metal layer and having a resistance value which varies depending on strain and a metal wire connected to the strain gauge, a first cover layer protecting the first sensor layer, a second metal layer formed on the bottom of the polymer layer, a second sensor layer including the strain gauge formed on the bottom of the second metal layer and having a resistance value which varies depending on strain and the metal wire connected to the strain gauge, and a second cover layer protecting the second sensor layer.

In an embodiment, the first sensor layer may include a first strain gauge, a first metal wire connected to each of one end and the other end of the first strain gauge, a second drain gauge, and a second metal wire connected to each of one end and the other end of the second strain gauge.

In an embodiment, the first strain gauge and the second strain gauge may be formed such that longitudinal axes of the first and second strain gauges have a predetermined angle with a vertical axis of a plane.

In an embodiment, the first strain gauge and the second strain gauge may be formed such that lengths of line widths of the stain gauges and lengths of gaps between lines are different from each other.

In an embodiment, the first sensor layer may include a first strain gauge, a first metal wire connected to each of one end and the other end of the first strain gauge, a second drain gauge, and a second metal wire connected to each of one end and the other end of the second strain gauge.

In an embodiment, the first strain gauge and the second strain gauge may be formed such that the longitudinal axes of the first and second strain gauges are orthogonal to each other.

In an embodiment, the flexible tactile sensor may further include a communication unit transmitting a sensing value output from the tactile sensor array.

Another aspect of the present invention provides a system for monitoring a state of a user, which includes: a smart bed transmitting state information of the user by sensing the state of the user; and a monitoring server monitoring the state of the user based on the state information of the user, which is received by the smart bed, in which the smart bed includes a mattress including at least one flexible tactile sensor sensing a state of a user who lies, and a bed frame loading the mattress, and the at least one flexible tactile sensor is positioned at a point corresponding to a specific portion of the user who lies on the mattress.

In an embodiment, the flexible tactile sensor may be positioned at a point corresponding to a chest of the user who lies on the mattress and positioned across the chest of the user.

In an embodiment, the flexible tactile sensor may be positioned across a heart of the user.

The flexible tactile sensor may sense a movement state of a chest of the user, and the monitoring server may monitor a breathing state of the user based on movement state information of the chest of the user.

In an embodiment, when a received state information value fluctuates to a predetermined value or more, the monitoring server may determine that a posture of the user is changed.

In an embodiment, the monitoring server may monitor a sleeping state of the user based on a breathing state of the user.

In an embodiment, the monitoring server may monitor the state monitoring result information to a terminal of the user.

In an embodiment, the monitoring server may monitor the state monitoring result information to a medical team.

Yet another aspect of the present invention provides a method for monitoring a state of a user, which includes: sensing, by a flexible tactile sensor provided on a mattress of a smart bed, the state of the user who lies; transmitting, by the flexible tactile sensor provided on the mattress, the sensed state information to a monitoring server; monitoring, by the monitoring server, the state of the user based on the received state information; and providing, by the monitoring server, monitoring result information.

A smart bed according to an embodiment of the present invention can detect a state of a user through a double-sided flexible tactile sensor comprising strain gauges on both sides of the sensor. A smart bed according to an embodiment of the present invention can detect and monitor the state of the user just in a state in which the user lies in a bed without the need of using a separate apparatus or performing a separate pre-procedure.

Since the smart bed according to an embodiment of the present invention measures the state of the user through a flexible tactile sensor which can be in direct contact with the user, the state of each user can be detected and monitored without being influenced by a motion of a next person. A smart bed, and a user state monitoring system and a user state monitoring method according to an embodiment of the present invention can monitor the state of the user such as breathing, heartbeat, whether the user moves, or the like without giving a sense of discomfort to the user.

DESCRIPTION OF EMBODIMENTS

Figure 1:
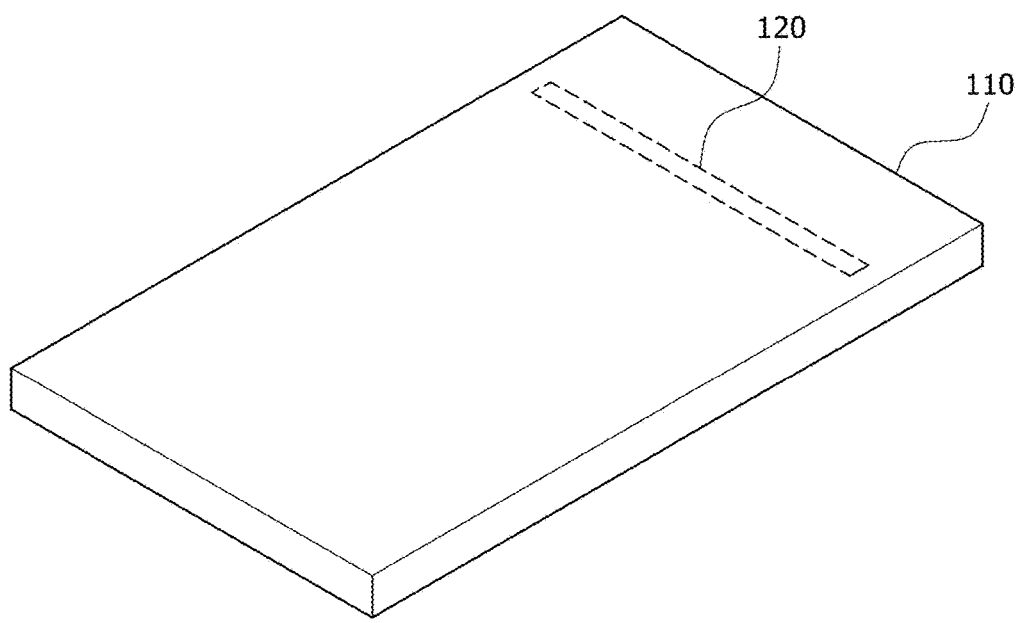
FIG. 1 is a diagram for describing a mattress that can sense a state of a user according to an embodiment of the present invention.

The scope of the present invention is not limited to the disclosed embodiments. That is, since embodiments of the invention can be variously changed and have various forms, the scope of the present invention should be understood to include equivalents capable of realizing the technical spirit. Further, it should be understood that since a specific embodiment should include all objects or effects or include only the effect, the scope of the present invention is limited by the object or effect.

Meanwhile, meanings of terms described in the present application should be understood as follows.

The terms "first," "second,", and the like are used to differentiate a certain component from other components, but the scope of should not be construed to be limited by the terms. For example, a first component may be referred to as a second component, and similarly, the second component may be referred to as the first component.

It should be understood that, when it is described that a component is "connected to" another component, the component may be directly connected to another component or a third component may be present therebetween. In contrast, it should be understood that, when it is described that an element is "directly connected to" another element, it is understood that no element is present between the element and another element. Meanwhile, other expressions describing the relationship of the components, that is, expressions such as "between" and "directly between" or "adjacent to" and "directly adjacent to" should be similarly interpreted.

It is to be understood that the singular expression encompass a plurality of expressions unless the context clearly dictates otherwise and it should be understood that term "include" or "have" indicates that a feature, a number, a step, an operation, a component, a part or the combination thereof described in the specification is present, but does not exclude a possibility of presence or addition of one or more other features, numbers, steps, operations, components, parts or combinations thereof, in advance.

In each step, reference numerals (e.g., a, b, c, etc.) are used for convenience of description, the reference numerals are not used to describe the order of the steps and unless otherwise stated, it may occur differently from the order specified. That is, the respective steps may be performed similarly to the specified order, performed substantially simultaneously, and performed in an opposite order.

The present invention can be implemented as a computer-readable code on a computer-readable recording medium and the computer-readable recording medium includes all types of recording devices for storing data that can be read by a computer system. Examples of the computer readable recording medium include a ROM, a RAM, a CD-ROM, a magnetic tape, a floppy disk, an optical data storage device, and the like and further include a device implemented as a type of a carrier wave (e.g., transmission through the Internet). Further, the computer readable recording media may be stored and executed as codes which may be distributed in the computer system connected through a network and read by a computer in a distribution method.

Logical blocks, modules or units described in connection with embodiments disclosed herein can be implemented or performed by a computing device having at least one processor, at least one memory and at least one communication interface. The elements of a method, process, or algorithm described in connection with embodiments disclosed herein can be embodied directly in hardware, in a software module executed by at least one processor, or in a combination of the two. Computer-executable instructions for implementing a method, process, or algorithm described in connection with embodiments disclosed herein can be stored in a non-transitory computer readable storage medium.

If it is not contrarily defined, all terms used herein have the same meanings as those generally understood by those skilled in the art. Terms which are defined in a generally used dictionary are interpreted to have the same meaning as the meaning in the context of the related art, and are not interpreted as an ideal meaning or excessively formal meanings unless clearly defined in the present application.

FIG. 1 is a diagram for describing a mattress that can sense a state of a user according to an embodiment of the present invention.

Referring to FIG. 1, the mattress includes a mattress body 110 and a flexible tactile sensor 120.

The mattress body 110 may be loaded on a bed. For example, the mattress body 110 is configured to be loaded in a bedroom bed, a patient bed, or the like, so that the user or a patient may lie and rest.

The flexible tactile sensor 120 is positioned on the mattress body 110 and detects a state of the user which lies on the mattress body. At least one flexible tactile sensor 120 may be positioned on the mattress body 110. In an embodiment, the flexible tactile sensor 120 may be positioned to be in direct contact with the user.

In an embodiment, the flexible tactile sensor 120 may be embedded in the mattress body 110. When the flexible tactile sensor 120 is embedded in the mattress body 110, the mattress body 110 protects the flexible tactile sensor 120, thereby enhancing durability and lifespan of the flexible tactile sensor 120. Further, since a position of the flexible tactile sensor 120 is not changed according to movement of the user, the flexible tactile sensor 120 may stably detect the state of the user.

In another embodiment, the flexible tactile sensor 120 may include a detachment/attachment portion on one surface and may be detached from/attached to the mattress body 110 through the detachment/attachment portion. When the flexible tactile sensor 120 is detached and attached from and to the mattress body 110, the flexible tactile sensor 120 may be positioned at a suitable position in consideration of a body condition of the user, a type of state information to be sensed, and the like. Further, a distance between the user and the flexible tactile sensor 120 may be shortened, so that the flexible tactile sensor 120 may accurately detect the state of the user.

The flexible tactile sensor 120 may be included in the mattress body 110 in various forms according to requirements. For example, the position, the number, and a shape of the flexible tactile sensor 120 may be determined depending on conditions including the body condition of the user, the type of the state information to be sensed, and the like and embedded in or detached from or attached to the mattress body 110.

Hereinafter, for easy description, it is assumed and described that the mattress body 110 includes one flexible tactile sensor 120.

In an embodiment, the flexible tactile sensor 120 is positioned at a point corresponding to a chest of the user which lies in the mattress body 110, but may be positioned across the chest of the user.

When the flexible tactile sensor 120 is positioned across the chest of the user, the flexible tactile sensor 120 may detect a movement state of the chest of the user. The flexible tactile sensor 120 may detect the movement of the chest of the user by detecting a pressure applied to the mattress as a volume of the chest increases or decreases by respiration, or the like.

In another embodiment, the flexible tactile sensor 120 is positioned at a point corresponding to an abdomen of the user which lies in the mattress body 110, but may be positioned across the abdomen of the user. The flexible tactile sensor 120 may detect the movement of the chest of the user by detecting a pressure applied to the mattress as a volume of the chest increases or decreases by respiration, or the like.

In another embodiment, the flexible tactile sensor 120 is positioned at the point corresponding to the chest of the user which lies in the mattress body 110, but may be positioned across a heart of the user. In this case, the flexible tactile sensor 120 may detect a heartbeat state of the user by detecting the pressure applied to the mattress according to a heartbeat.

Although it is assumed that one flexible tactile sensor 120 is positioned in the mattress body 110, the flexible tactile sensors may be positioned at the points corresponding to the chest, the abdomen, and the heart of the user, respectively. In addition, the flexible tactile sensor 120 may be positioned to cross a specific portion of the user in a transverse direction, or may be positioned to cross the specific portion in a longitudinal direction. A shape of the flexible tactile sensor 120 may be a line shape or a shape corresponding to a portion to be measured.

Figure 2:
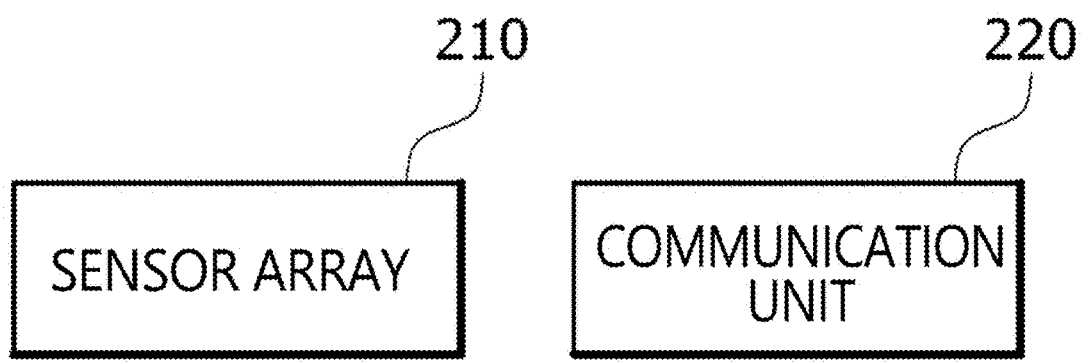
FIG. 2 is a block diagram illustrating a configuration of a flexible tactile sensor illustrated in FIG. 1.

FIG. 2 is a block diagram illustrating a configuration of a flexible tactile sensor illustrated in FIG. 1.

Referring to FIG. 2, the flexible tactile sensor 120 includes a tactile sensor array 210 including a plurality of tactile sensor modules and a communication unit 220 transmitting state information (sensing value) output from the tactile sensor array 210 in a wired or wireless method.

For example, the communication unit 220 may transmit the state information to a monitoring server using a wireless communication means such as Bluetooth, wireless LAN, or short-range wireless communication.

In an embodiment, the flexible tactile sensor 120 may further include a temperature measuring means and measure a body temperature of the user through the temperature measuring means. The measured body temperature may be used to correct the sensing value. For example, the monitoring server may correct the sensing value based on resistance characteristics depending on the measured body temperature and the temperature of the sensor.

In another embodiment, the body temperature of the user may be measured based on the sensing value of the flexible tactile sensor 120 and the resistance characteristic depending on the temperature of the sensor. For example, the monitoring server may measure the body temperature based on the sensing value measured in a specific state and the resistance characteristic depending on the temperature of the corresponding sensor in the corresponding state.

Figure 3:
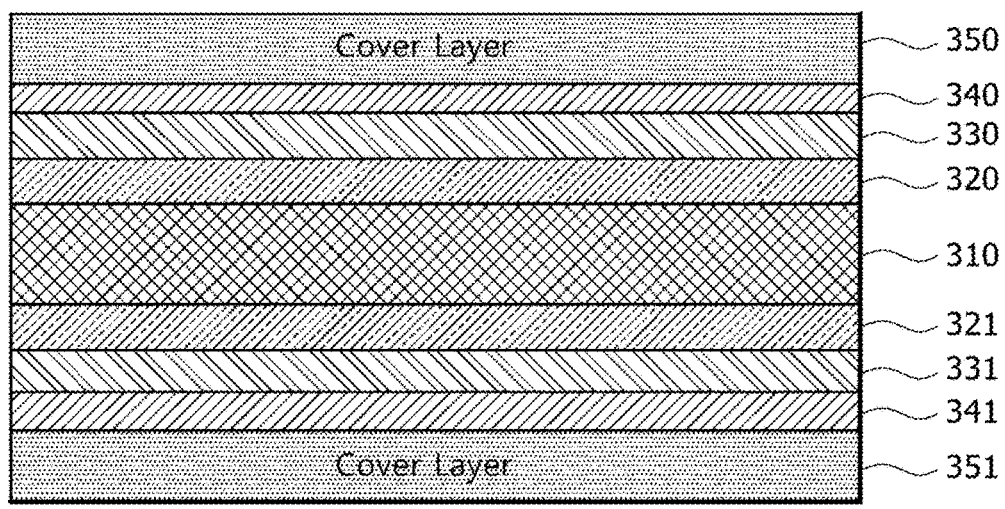
FIG. 3 is a schematic cross-sectional view of a tactile sensor module included in the flexile tactile sensor illustrated in FIG. 2.

FIG. 3 is a schematic cross-sectional view of a tactile sensor module included in the flexile tactile sensor illustrated in FIG. 2.

Referring to FIG. 3, the flexible tactile sensor module includes a polymer layer 310, a first metal layer 320 formed on the top of the polymer layer 310, a first sensor layer 330 including a strain gauge formed on the top of the first metal layer 320 and having a resistance value which varies depending on strain and a metal wire connected to the strain gauge, a first cover layer 350 protecting the first sensor layer 330, a second metal layer 321 formed on the bottom of the polymer layer 310, a second sensor layer 331 including the strain gauge formed on the bottom of the second metal layer 321 and having the resistance value which varies depending on strain and the metal wire connected to the strain gauge, and a second cover layer 351 protecting the second sensor layer 331.

The polymer layer 310 may be flexibly bent to external force while maintaining a structure of a sensor. In an embodiment, the polymer layer 310 may be a polyimide (PI) layer. Polyimide has high thermal stability, stable physical and chemical properties, is thin, and has excellent flexibility. In an embodiment, the polymer layer 310 may be formed with a thickness of 25 μm.

The first metal layer 320 and the second metal layer 321 are formed on the top (alternatively, outward) and the bottom (alternatively, outward) of the polymer layer 310, respectively. The first metal layer 320 and the second metal layer 321 may be formed by depositing nickel-chromium (Ni—Cr) on the upper and lower parts of the polymer layer 310. In an embodiment, each of the first metal layer 320 and the second metal layer 321 may be formed with a thickness of 400 ÅA. In an embodiment, the first metal layer 320 and the second metal layer 321 may be deposited only at a location where the strain gauge is to be patterned.

The first sensor layer 330 includes the strain gauge formed above the first metal layer 320 and having the resistance value which varies depending on the strain and the metal wire connected to the strain gauge. The strain gauge may be patterned on the top of the first metal layer 320 and thereafter, the metal wire may be connected to the strain gauge. The metal wires are connected to one end and the other end of the strain gauge, respectively to be connected to the first and second electrodes. The metal wire is patterned with copper (Cu) to be connected to the strain gauge. In an embodiment, the first sensor layer 330 may be formed with a thickness of 13 μm.

The second sensor layer 331 includes the strain gauge formed on the bottom of the second metal layer 321 and having the resistance value which varies depending on the strain and the metal wire connected to the strain gauge. A description of the second sensor layer 331 is the same as that of the first sensor layer 330.

The first cover layer 350 protecting the first sensor layer 330 may be formed on top of the first sensor layer 330 and the second cover layer 351 protecting the second sensor layer 331 may be formed on the bottom of the second sensor layer 331. In an embodiment, the cover layers 350 and 351 may be polyester (PET) layers.

A first adhesive layer 340 may be formed on the top of the first sensor layer 330 and the first cover layer 350 may be bonded to the top of the first sensor layer 330 through the first adhesive layer 340. Similarly, a second adhesive layer 341 may be formed on the bottom of the second sensor layer 331 and the second cover layer 351 may be bonded to the bottom of the second sensor layer 331 through the second adhesive layer 341. For example, the cover layers 350 and 351 may be bonded after applying an adhesive to the sensor layers 330 and 331 or attaching an adhesive film.

The flexible tactile sensor of FIG. 3 includes sensors on both surfaces to sense force on both surfaces. For example, when the flexible tactile sensor is bent to one side by external force, bending the flexible tactile sensor may be sensed on both surfaces (bending up and bending down), thereby increasing accuracy of the sensing. Further, the flexible tactile sensor may measure normal force applied to one point of the corresponding tactile sensor.

Figure 4:
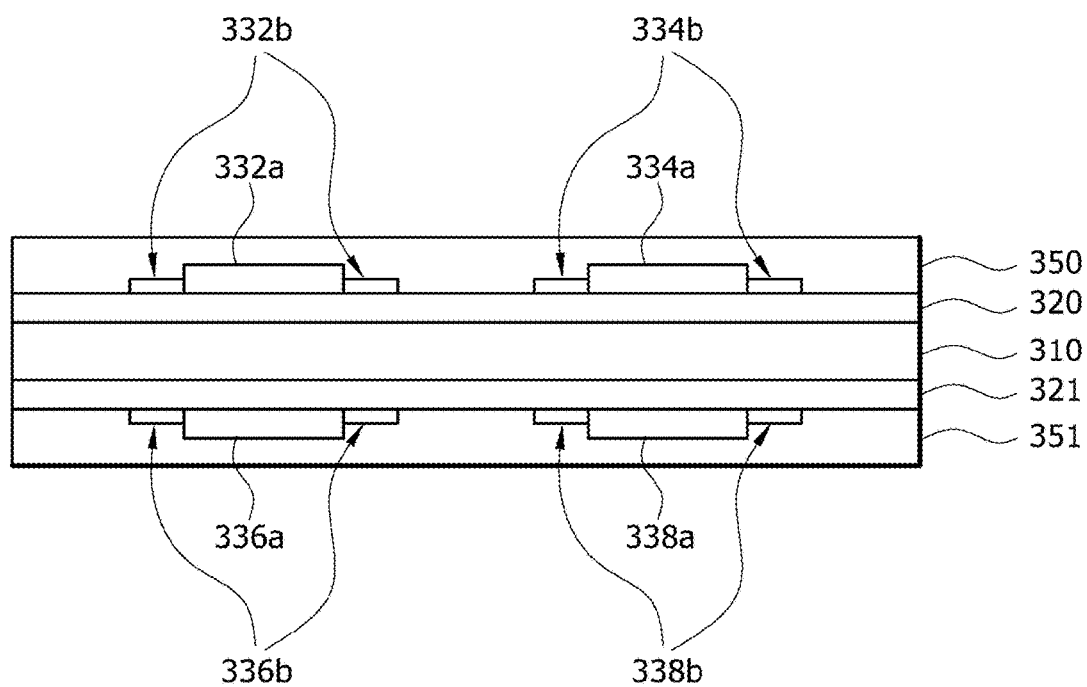
FIG. 4 is a specific cross-sectional view of the tactile sensor module illustrated in FIG. 3.

FIG. 4 is a specific cross-sectional view of the tactile sensor module illustrated in FIG. 3.

Referring to FIG. 4, the first sensor layer 330 includes a first strain gauge 332a, a first metal wire 332b connected to each of one end and the other end of the first strain gauge 332a, a second strain gauge 334a, and a second metal wire 334b connected to each of one end and the other end of the second strain gauge 334a. The first strain gauge 332a and the second strain gauge 334a may be formed to be spaced apart from each other.

In an embodiment, the first strain gauge 332a and the first metal wire 332b may correspond to driving sensor modules and the second strain gauge 334a and the second metal wire 334b may correspond to correction sensor modules. For example, the first strain gauge 332a may output a first sensing value via the first metal wire 332b and output a second sensing value for correcting the first sensing value through the second metal wire 334b.

For example, a metal strain gauge may have a resistance characteristic that resistance linearly increases as a temperature rises. Accordingly, the monitoring server (or a manager) includes a module or algorithm for correcting the sensing value, and the monitoring server (or the manager) may correct an error of the sensing value by a temperature difference between the sensor modules by using the first sensing value output from the driving sensor module and the second sensing value output from the correction sensor module.

The second sensor layer 332 includes a third strain gauge 336a, a third metal wire 336b connected to each of one end and the other end of the third strain gauge 336a, a fourth strain gauge 338a, and a fourth metal wire 338b connected to each of one end and the other end of the fourth strain gauge 338a. The third strain gauge 336a and the fourth strain gauge 338a may be formed to be spaced apart from each other.

In an embodiment, the third strain gauge 336a and the third metal wire 336b may correspond to the driving sensor modules and the fourth strain gauge 338a and the fourth metal wire 338b may correspond to the correction sensor modules. For example, the third strain gauge 336a may output a third sensing value through the first metal wire 336b and output a fourth sensing value for correcting the third sensing value through the fourth metal wire 338b.

In an embodiment, the first metal layer and the second metal layer may be deposited over the polymer layer 310 and may be deposited only at locations 320a, 320b, 321a, and 321b where the strain gauge is patterned.

Figure 5:
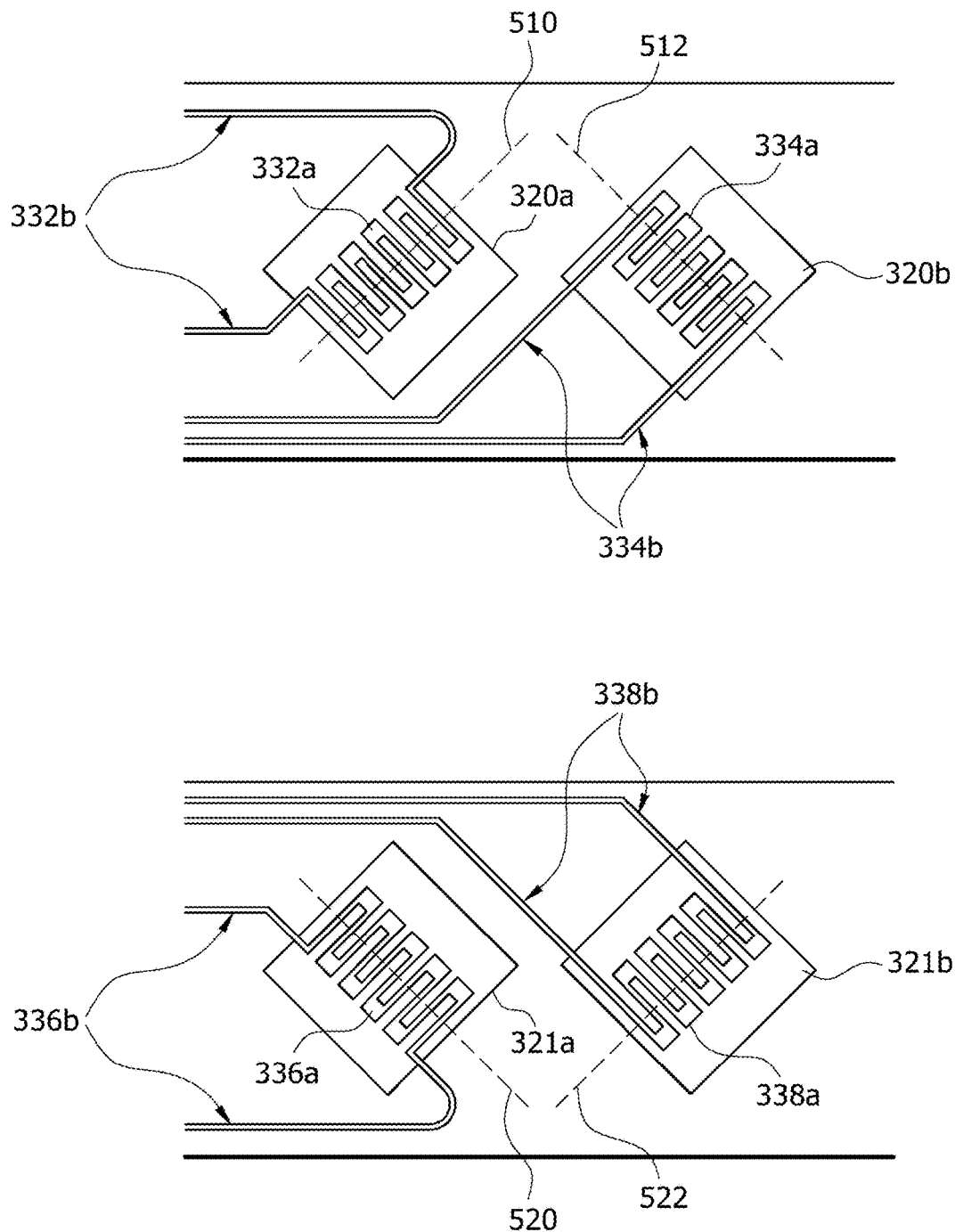
FIG. 5 is a diagram for describing a strain gauge and a metal wire of the tactile sensor module illustrated in FIG. 4.

FIG. 5 is a diagram for describing a strain gauge and a metal wire of the tactile sensor module illustrated in FIG. 4.

Referring to FIG. 5, the strain gauges 332a, 334a, 336a, and 338a may be patterned in a continuous '⊇' shape. Each metal wire may be connected to the end of each strain gauge.

In an embodiment, lengths of line widths and lengths of gaps between lines of the strain gauges 332a and 336a of the driving sensor module and the strain gauges 334a and 338a of the correction sensor module may be different from each other. The length of the line width and the length of the gap between the lines may be implemented to be different according to an application target of the sensor or a main measurement direction of the force.

For example, a width of lines (line patterns) of the strain gauges 332a and 336a of the driving sensor module may be in a range of 40 μm to 90 μm, a gap between two immediately neighboring lines (line patterns) may be in a range of 110 μm to 160 μm, a width of lines of the strain gauges 334a and 338a of the correction sensor module may be in a range of 50 μm to 100 μm, and a gap between the two immediately neighboring lines may be in a range of 100 μm to 150 μm.

In an embodiment, a width of lines (line patterns) of the strain gauges 332a and 336a of the driving sensor module is 65 μm, a gap between two immediately neighboring lines is 135 μm, a width of lines of the strain gauges 334a and 338a of the correction sensor module is 75 μm, and a gap between two immediately neighboring lines is 125 μm.

In an embodiment, the strain gauges 332a, 334a, 336a, and 338a may be formed in a direction to easily measure the bending force or the normal force. For example, the strain gauges 332a, 334a, 336a, and 338a may be formed so that an expected folding line or bending line of the flexible tactile sensor becomes parallel to longitudinal axes 510, 512, 520, and 522 of the strain gauges 332a, 334a, 336a, and 338a. As the folding line or bending line of the flexible tactile sensor becomes parallel to the longitudinal axes 510, 512, 520, and 522 of the strain gauges 332a, 334a, 336a, and 338a, strain rate of the strain gauge becomes larger and measurement accuracy may be thus increased. In an embodiment, the expected folding line or bending line of the flexible tactile sensor may be assumed by a designer in advance by considering an application target, an application location, or force to be measured and the strain gauges 332a, 334a, 336a, and 338a may be formed based on the assumption.

For example, in FIG. 5, the first strain gauge 332a of the driving sensor module and the second strain gauge 334a of the correction sensor module may be formed such that each of the longitudinal axes 510 and 512 has a predetermined angle with a vertical axis of a plane (e.g., when viewed over the top, in a direction perpendicular to a major surface of the polymer layer. For example, the first strain gauge 332a and the second strain gauge 334a may be formed to be oblique to each other.

In an embodiment, the first strain gauge 332a and the second strain gauge 334a are spaced apart from each other and the respective longitudinal axes 510 and 512 cross each other to be formed to have a shape of '∧'.

The third strain gauge 336a of the driving sensor module and the fourth strain gauge 338a of the correction sensor module may be formed such that each of the longitudinal axes 520 and 522 has a predetermined angle with the vertical axis of the plane. For example, the third strain gauge 336a and the fourth strain gauge 338a may be formed to be oblique to each other.

In an embodiment, the third strain gauge 336a and the fourth strain gauge 338a are spaced apart from each other and the respective longitudinal axes 520 and 522 cross each other to be formed to have the shape of '∨'.

In an embodiment, the first strain gauge 332a and the third strain gauge 336a may be formed at opposite locations corresponding to each other and the second strain gauge 334a and the fourth strain gauge 338a may be formed at opposite locations corresponding to each other. In another embodiment, the first strain gauge 332a and the second strain gauge 334a at one side and the third strain gauge 336a and the fourth strain gauge 338a may be formed to cross each other. For example, the first strain gauge 332a, the third strain gauge 336a, the second strain gauge 334a, and the fourth strain gauge 338a may be formed to cross each other in order.

In the flexible tactile sensor configured as above, the sensors are provided on both surfaces to accurately sense the force on both surfaces.

Figure 6:
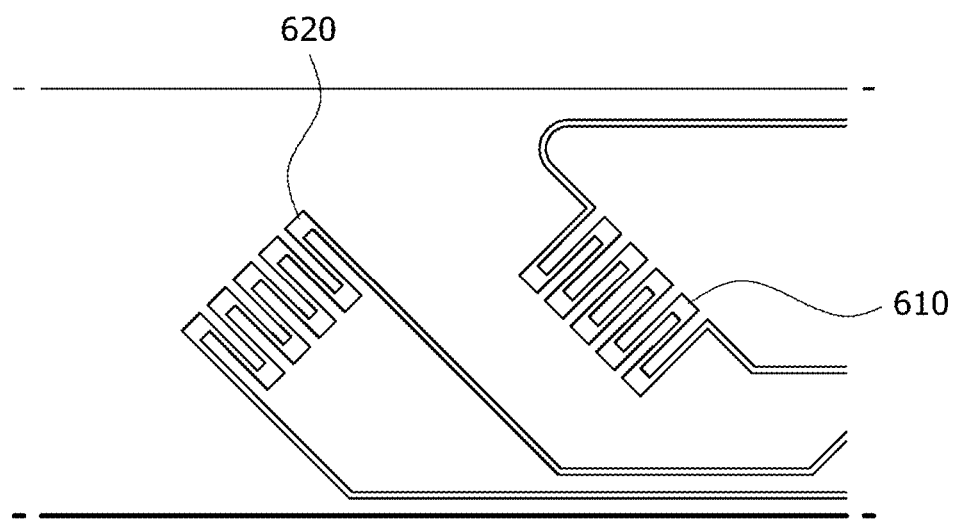
FIG. 6 is a diagram illustrating an implementation example of the tactile sensor module illustrated in FIG. 4.

FIG. 6 is a diagram illustrating an implementation example of the tactile sensor module illustrated in FIG. 4.

Referring to FIG. 6, it can be seen that a driving sensor module 610 and a correction sensor module 620 are formed on one side of the flexible tactile sensor. The strain gauges of the tactile sensor module may be formed on the same surface or on different surfaces as illustrated in FIG. 6.

Figure 7A:
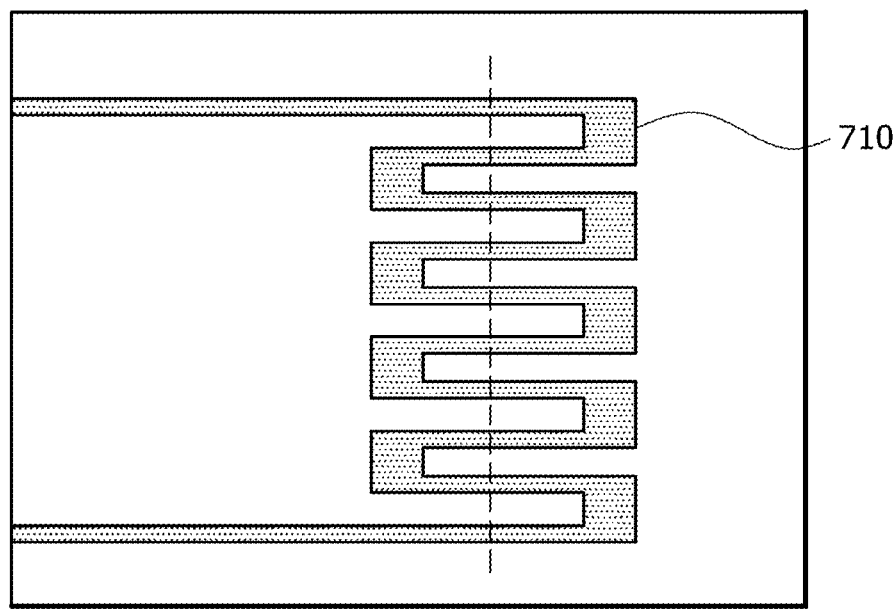
FIGS. 7A and 7B illustrate another implementation example of the tactile sensor module.
Figure 7B:
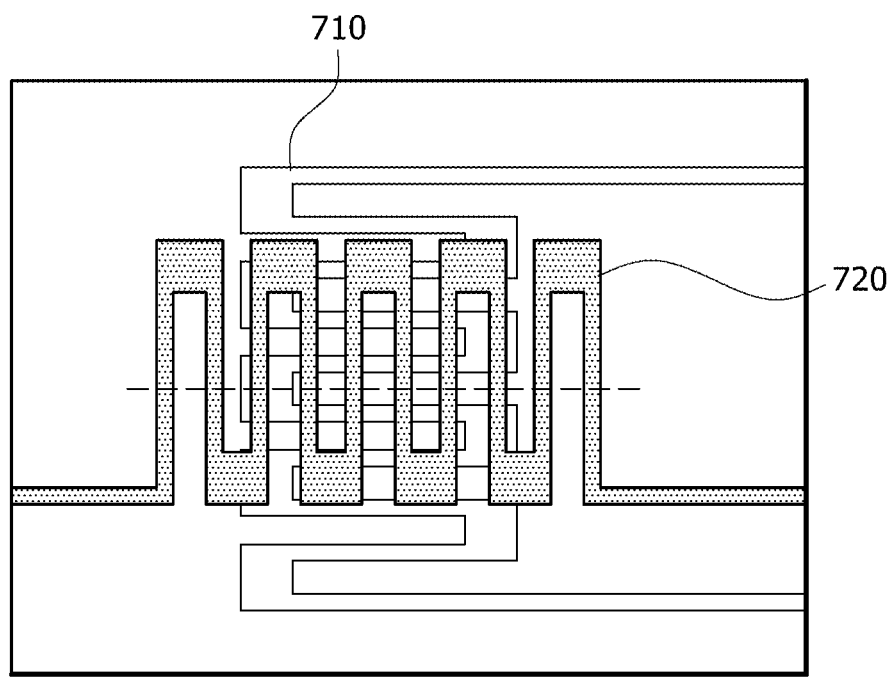

FIGS. 7A and 7B illustrate another implementation example of the tactile sensor module.

Referring to FIGS. 7A and 7B, a first strain gauge 710 may be formed on a first surface (FIG. 7A) and a second strain gauge 720 may be formed on a second surface (an opposite surface of the first surface) (FIG. 7B). In an embodiment, the first strain gauge 710 and the second strain gauge 720 may be formed such that the respective longitudinal axes are perpendicular to each other. In another embodiment, the first strain gauge 710 and the second strain gauge 720 may be formed such that the respective longitudinal axes are cross obliquely to each other.

For example, in FIGS. 7A and 7B, the first strain gauge 710 may be formed such that the longitudinal axis is perpendicular to a horizontal plane of the first surface (FIG. 7A) and the second strain gauge 720 may be formed such that the longitudinal axis is parallel to the horizontal plane of the second surface (FIG. 7B) and perpendicular to each other. Through the tactile sensor module formed as described above, a user may confirm a strain direction according to applied force.

In an embodiment, the first strain gauge 710 may correspond to the strain gauge of a first driving sensor module and the second strain gauge 720 may correspond to the strain gauge of a second driving sensor module. In this case, the monitoring server (or the manager) may include a module or algorithm for correcting the sensing value in a predetermined manner and may correct the sensing value output from each driving sensor module.

In another embodiment, the first strain gauge 710 may correspond to the strain gauge of the driving sensor module and the second strain gauge 720 may correspond to the strain gauge of the correction sensor module.

Figure 8:
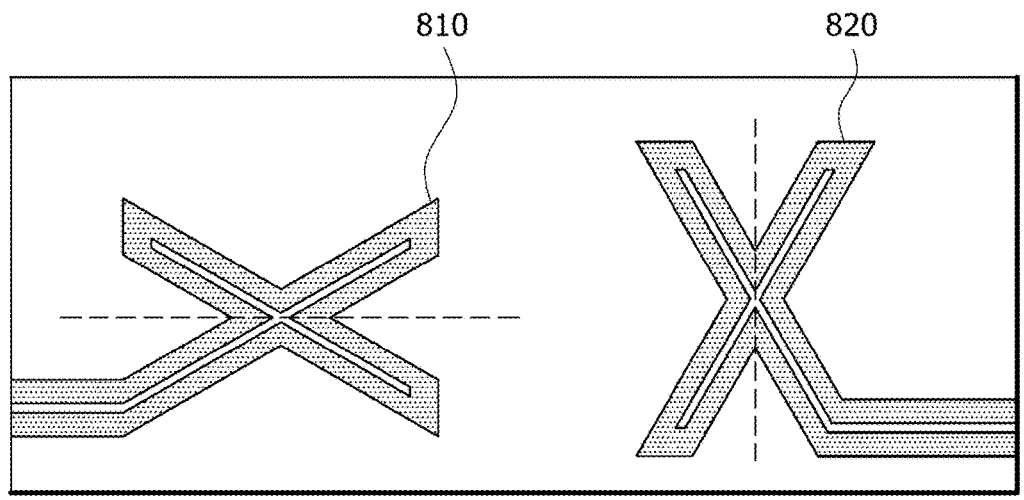
FIG. 8 is a diagram illustrating yet another implementation example of the tactile sensor module.

FIG. 8 is a diagram illustrating yet another implementation example of the tactile sensor module.

Referring to FIG. 8, a first strain gauge 810 and a second strain gauge 820 may be formed on the same plane. In another embodiment, the first strain gauge 810 and the second strain gauge 820 may be formed on different surfaces.

Each of the strain gauges 810 and 820 may be patterned in an 'X' shape and metal wires may be connected to ends of the strain gages 810 and 820, respectively.

In an embodiment, the longitudinal axis of the first strain gauge 810 and the longitudinal axis of the second strain gauge 820 may be formed to be different directions. For example, in FIG. 8, the first strain gauge 810 may be formed such that the longitudinal axis is parallel to the horizontal plane of the corresponding surface and the second strain gauge 820 may be formed such that the longitudinal axis is perpendicular to the horizontal surface of the corresponding surface. In another embodiment, the longitudinal axis of the first strain gauge 810 and the longitudinal axis of the second strain gauge 820 may be formed to be the same direction.

In an embodiment, the first strain gauge 810 may correspond to the strain gauge of the first driving sensor module and the second strain gauge 820 may correspond to the strain gauge of the second driving sensor module. In this case, the monitoring server (or the manager) may include a module or algorithm for correcting the sensing value in a predetermined manner and may correct the sensing value output from each driving sensor module.

In another embodiment, the first strain gauge 810 may correspond to the strain gauge of the driving sensor module and the second strain gauge 820 may correspond to the strain gauge of the correction sensor module.

In the embodiments of FIGS. 6 to 8, each flexible tactile sensor includes strain gauges of the same pattern, but one flexible tactile sensor may include strain gauges of different patterns.

For example, one flexible tactile sensor may include both a strain gauge of a continuous 2 shape and a strain gauge having an 'X' shape.

Figure 9:
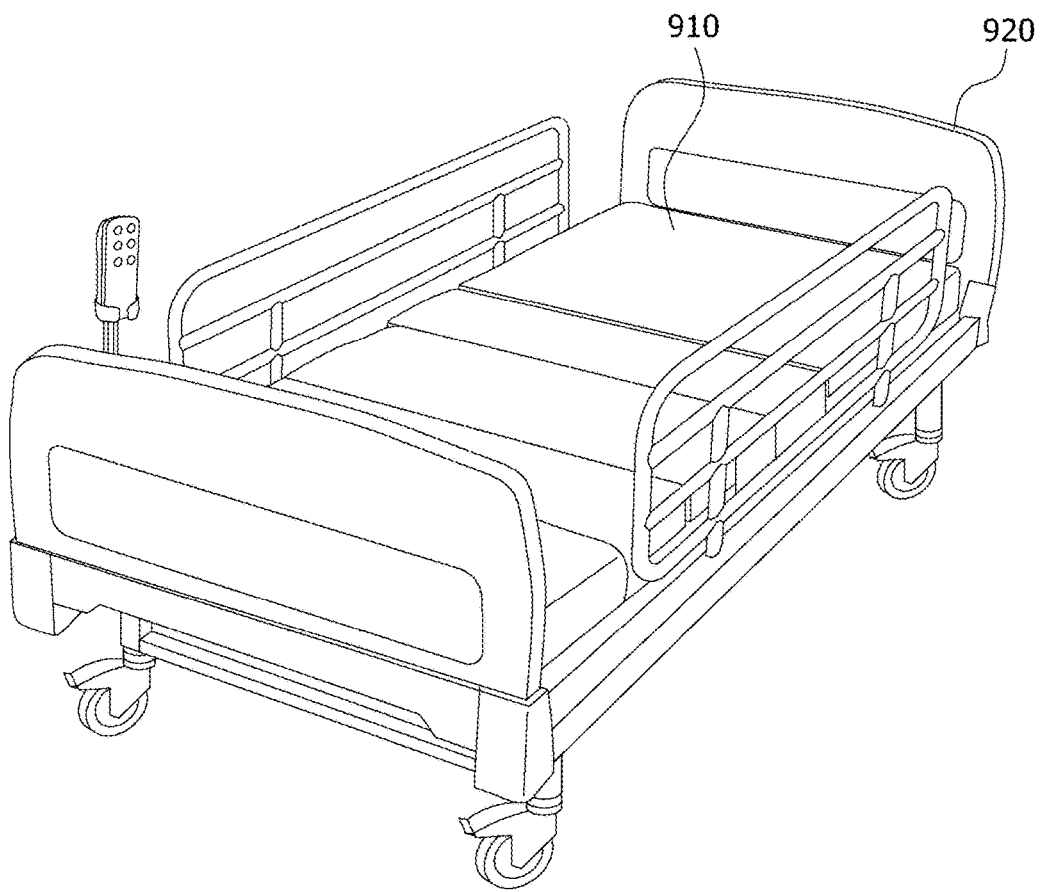
FIG. 9 is a diagram illustrating an example of a smart bed including the mattress illustrated in FIG. 1.

FIG. 9 is a diagram illustrating an example of a smart bed including the mattress illustrated in FIG. 1.

Referring to FIG. 9, the smart bed includes a mattress 910 including at least one flexible tactile sensor for sensing the state of the user who lies and a bed frame 920 accommodating or supporting the mattress 910. The mattress 910 includes a mattress body 110 and at least one flexible tactile sensor 120 positioned in the mattress body 110.

The smart bed may sense the state of the user using at least one flexible tactile sensor and transmit the sensed state information to the server.

Figure 10:
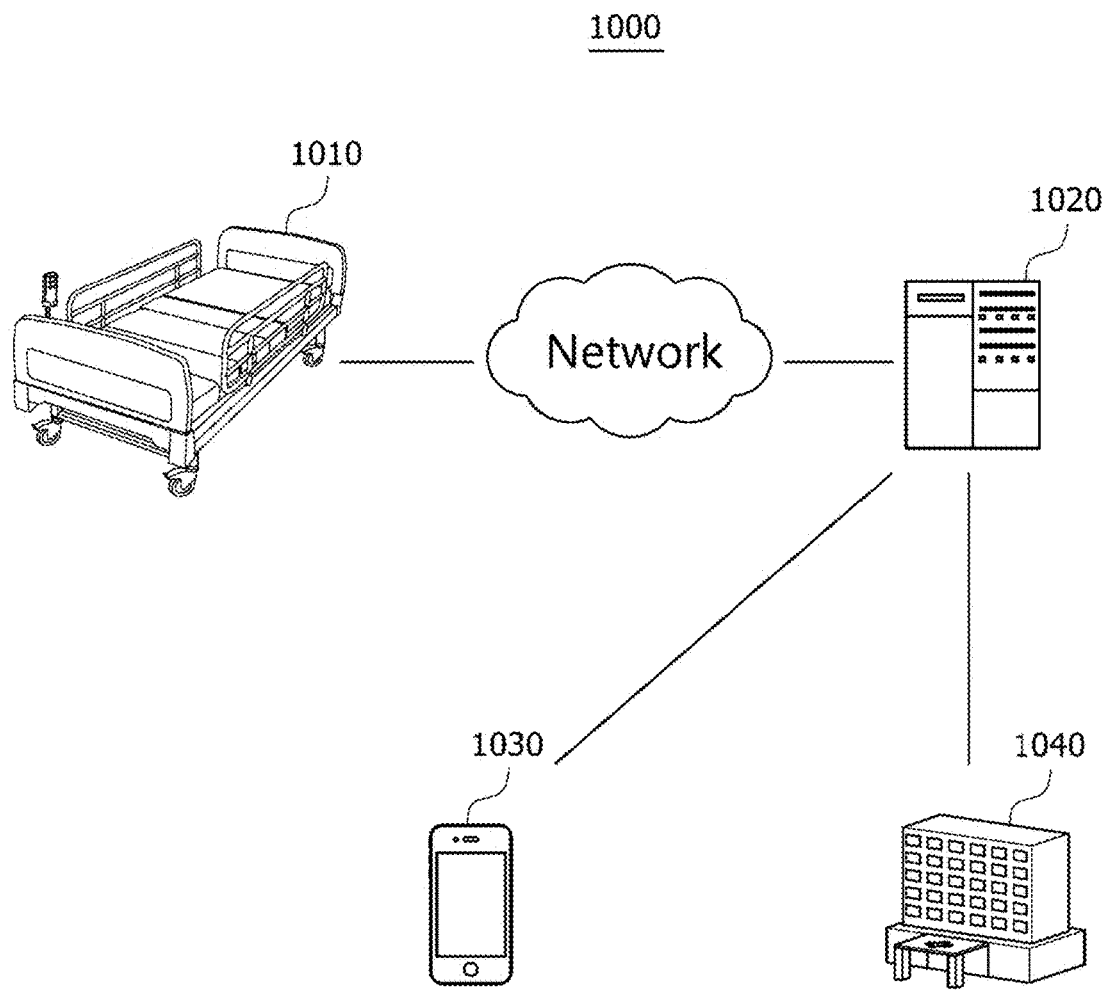
FIG. 10 is a diagram for describing a user state monitoring system according to an embodiment of the present invention.

FIG. 10 is a diagram for describing a user state monitoring system according to an embodiment of the present invention.

Referring to FIG. 10, the user state monitoring system 1000 includes a smart bed 1010, a monitoring server 1020, a user terminal 1030, and a medical team terminal 1040.

The smart bed 1010 senses the state of the user using at least one flexible tactile sensor and transmits the sensed state information to the monitoring server 1020 through a network. The monitoring server 1020 analyzes and monitors the state of the user based on the state information of the user received from the smart bed 1010.

For example, when the flexible tactile sensor is positioned at a point corresponding to the chest of the user who lies on the mattress, but positioned across the chest of the user, the flexible tactile sensor senses the movement state of the chest of the user and transmits the sensed movement state to the monitoring server 1020. The flexible tactile sensor may senses the pressure applied to the mattress as the volume of the chest increases or decreases and sense the movement state of the chest of the user.

The monitoring server 1020 may analyze and monitor a breathing state of the user based on the movement state information of the chest, which is received by the flexible tactile sensor of the smart bed 1010.

Figure 11A:
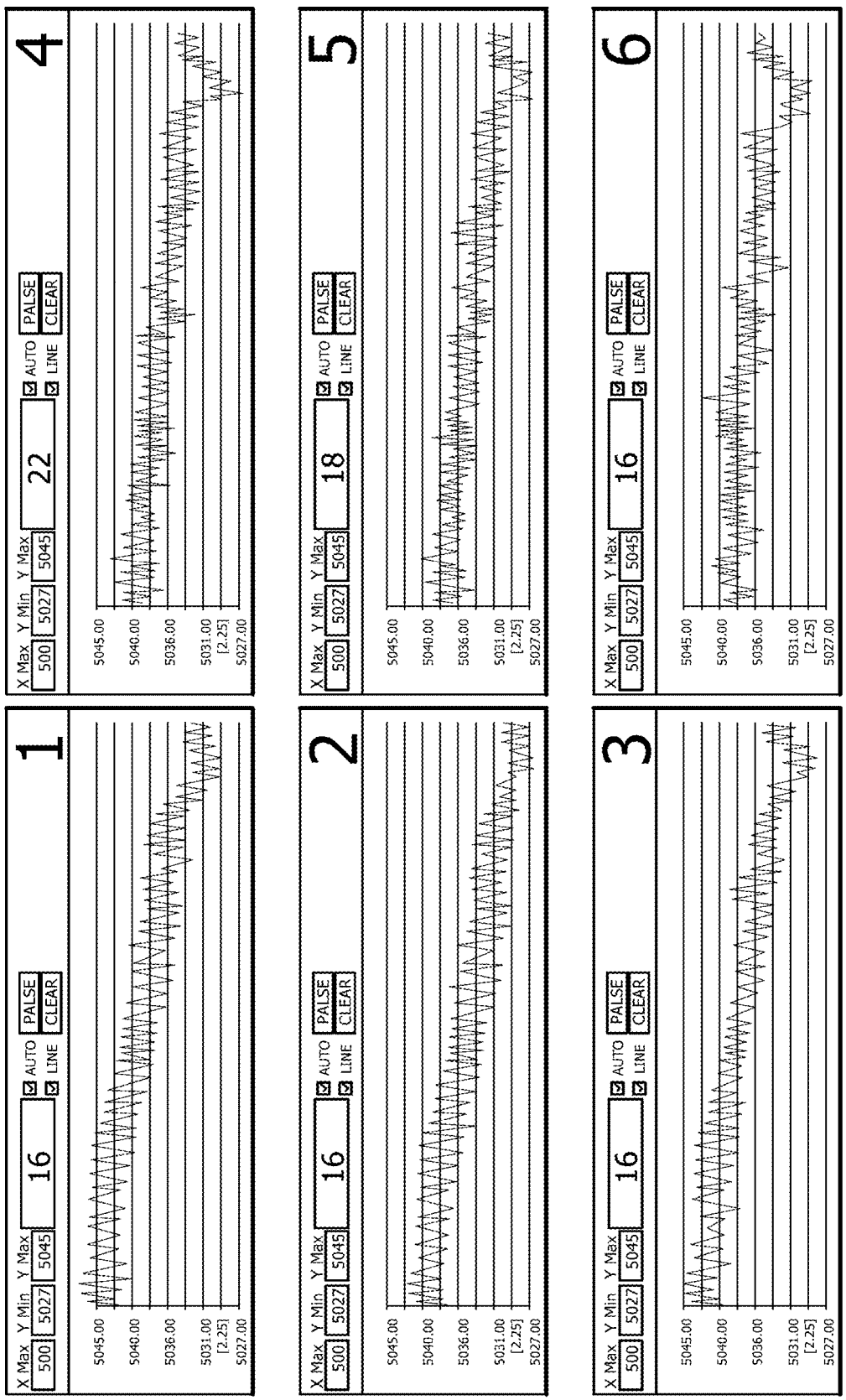
FIGS. 11A and 11B are diagram illustrating an example of analyzing the state of the user in a monitoring server illustrated in FIG. 10.
Figure 11B:
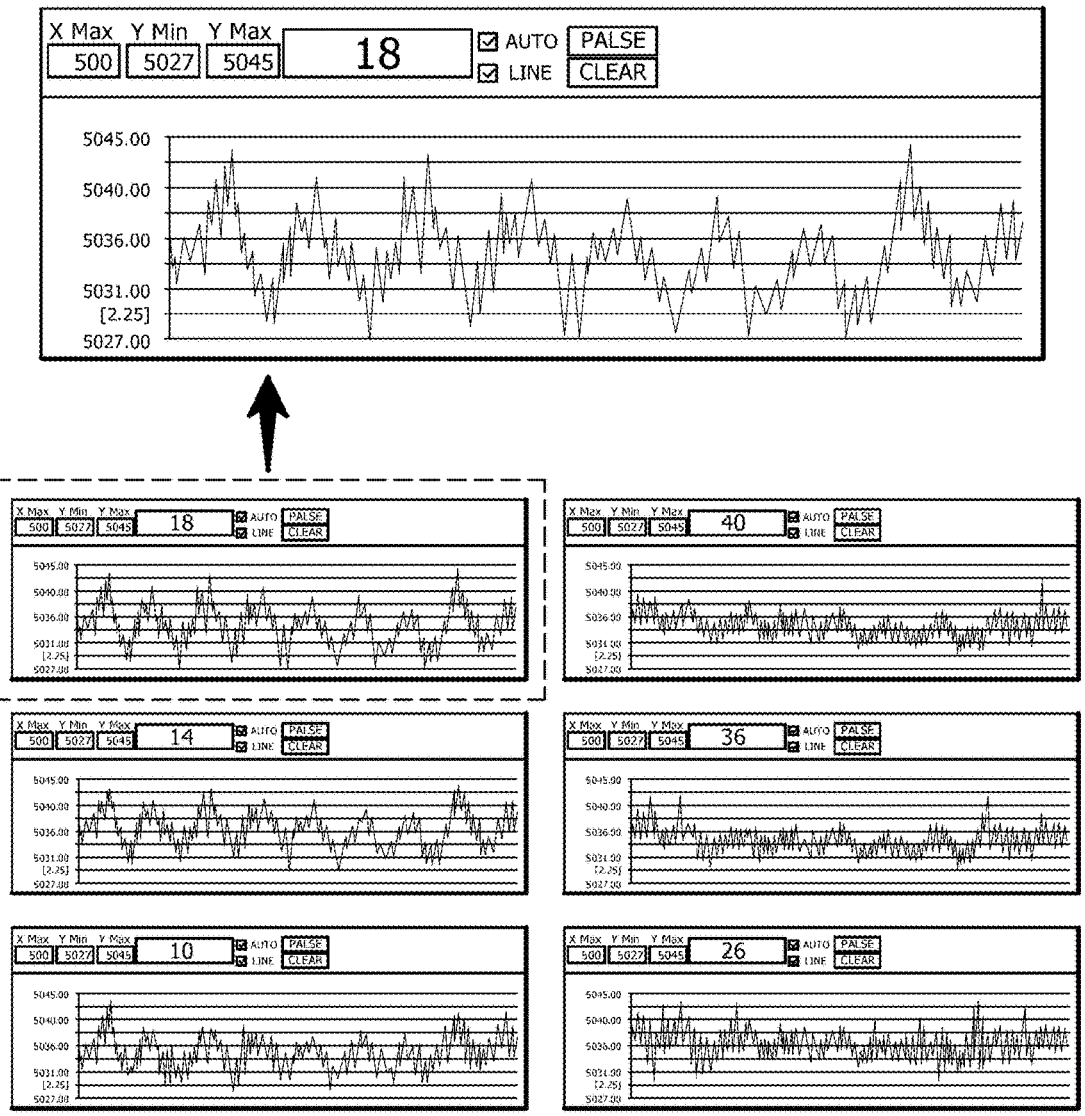

FIGS. 11A and 11B are diagram illustrating an example of analyzing the state of the user in a monitoring server illustrated in FIG. 10.

FIG. 11A is a diagram illustrating the sensing value received by the flexible tactile sensor when no one lies on the mattress. FIG. 11A illustrates an example of a case where a sensor array of the flexible tactile sensor is constituted by six sensor modules and when no one lies on the mattress, no pattern is shown except for noise in the sensing values received by six sensor modules.

FIG. 11B is a diagram illustrating the sensing value received by the flexible tactile sensor when the user lies on the mattress. Referring to FIG. 11B, it can be seen that the sensing values received by six sensor modules are periodically changed according to the breathing of the user.

That is, the monitoring server 1020 may analyze the breathing state of the user and monitor the breathing state based on the movement state information of the chest of the user, which is received by the flexible tactile sensor. For example, the monitoring server 1020 may analyze respiration rate per minute, whether the respiration is normal, whether irregular respiration occurs, and the like and monitor the breathing state of the user based on an analysis result.

In an embodiment, the monitoring server 1020 may analyze other state information (e.g., another vital sign of the user, etc.) associated with the breathing state of the user. For example, the monitoring server 1020 may analyze the heartbeat state of the user based on an association between the breathing state and the heartbeat state. The monitoring server 1020 may monitor a sleeping state of the user based on the breathing state of the user. For example, when two persons lie on a bed for two persons, the state of each user is measured through the flexible tactile sensor, so that the sleeping state of each user may be monitored without being influenced by the movement of a person next to the bed.

In an embodiment, when the state information value received by the flexible tactile sensor of the smart bed 1010 varies to a predetermined value or more, the monitoring server 1020 may determine that the user changes a posture thereof.

In another embodiment, when the state information value received by the flexible tactile sensor of the smart bed 1010 fluctuates to a predetermined value or more or returns to a value of a state in which the pressure is not applied, the monitoring server 1020 may determine that a bed user (e.g., a patent or an elderly person) is out of the bed. For example, when a patient or an elderly patient having an uncomfortable behavior lies on the smart bed 1010 and then, wakes up, the state information value received by the flexible tactile sensor may fluctuate to a predetermined value or more or return to a value of a state in which the pressure is not applied.

In this case, the monitoring server 1020 may notify a guardian terminal or the medical team terminal that the bed user (for example, the patient or the elderly person) is out of the bed. For example, when it is determined that a bed user (e.g., a demented elderly person) is out of the bed, the monitoring server 1020 may transmit a message to a terminal of a predetermined guardian or make a call.

Figure 12A:
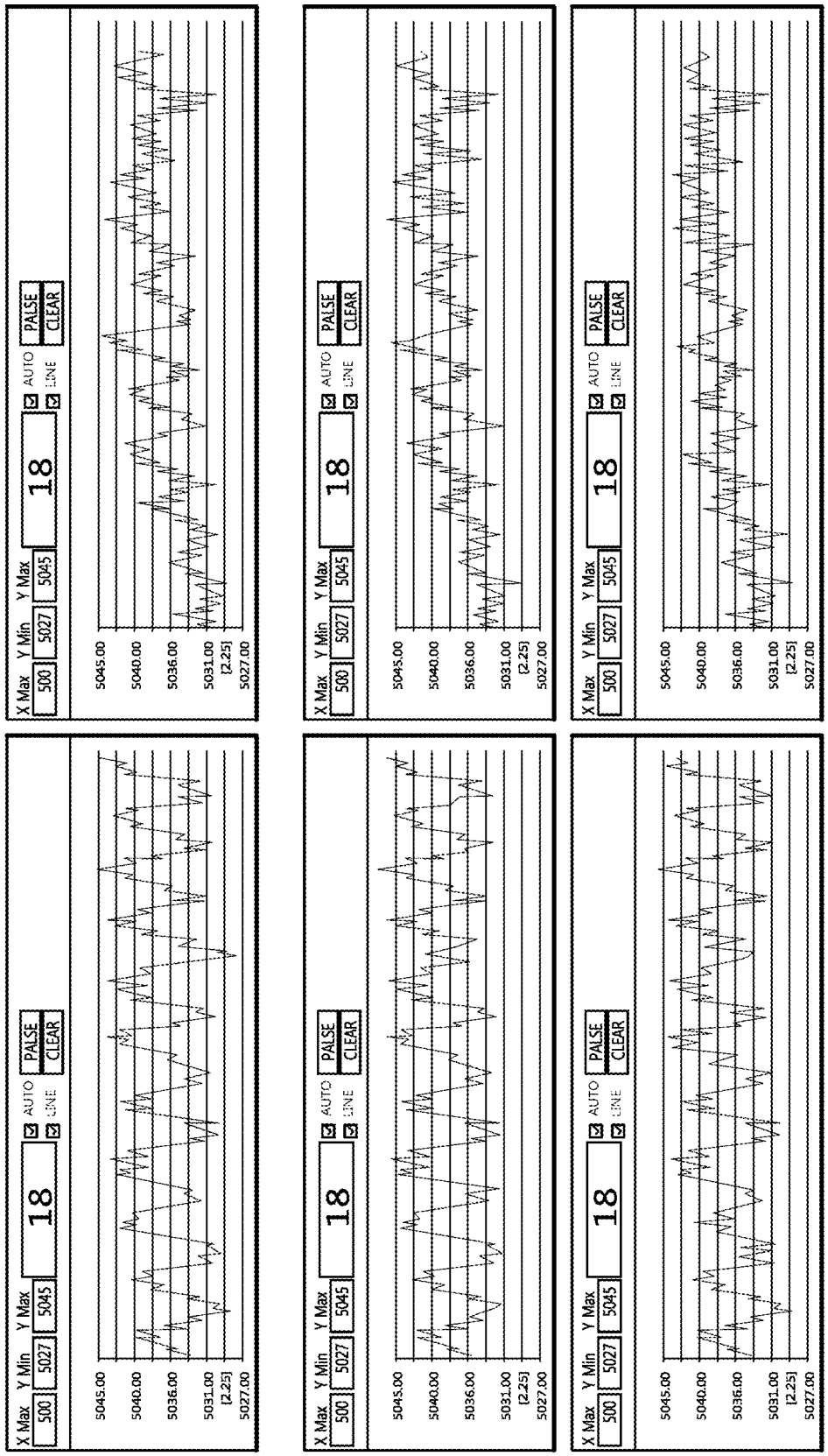
FIGS. 12A, 12B and 12C illustrate an example of analyzing whether a posture of a user is changed in the monitoring server illustrated in FIG. 10.
Figure 12B:
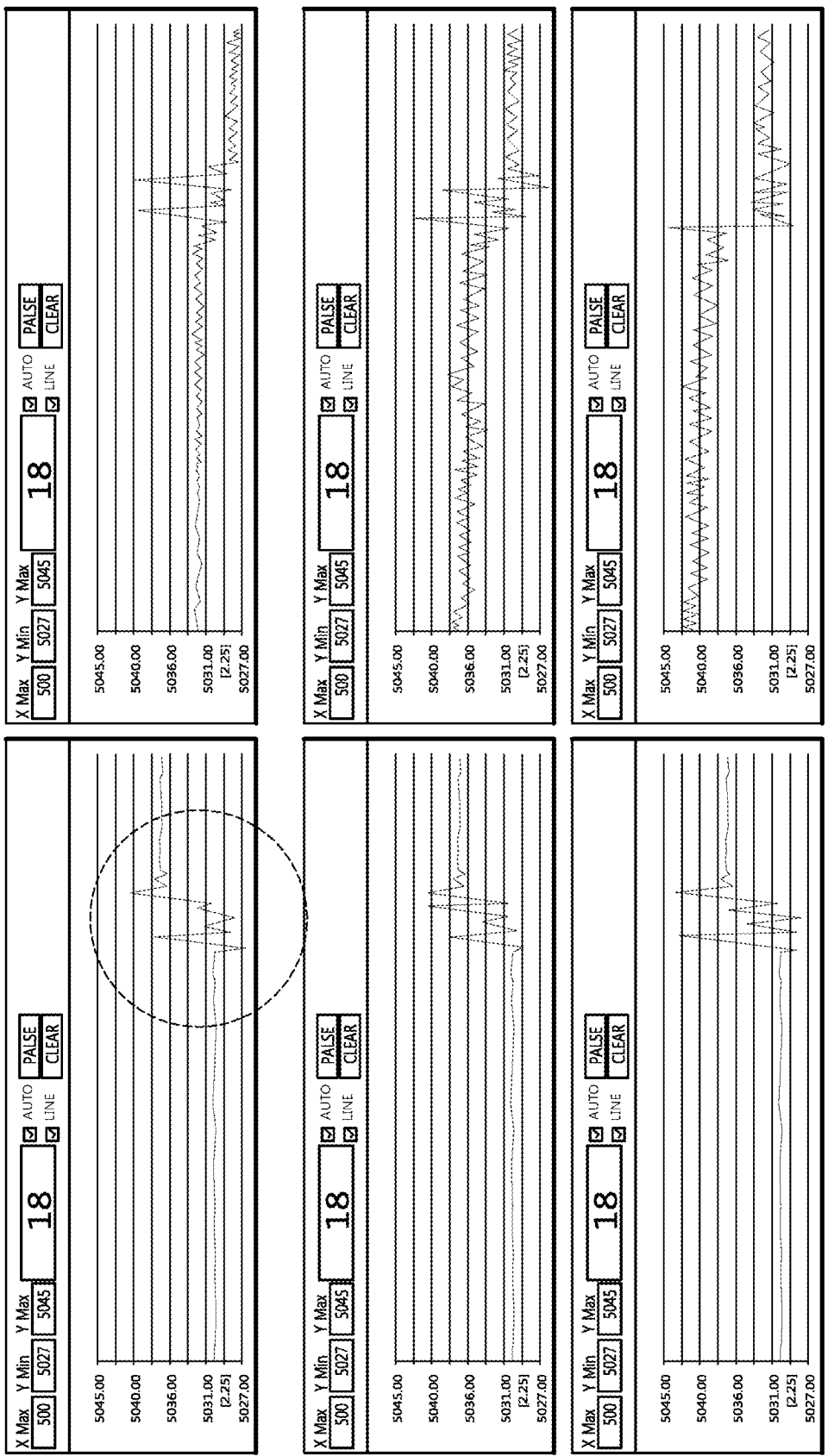
Figure 12C:
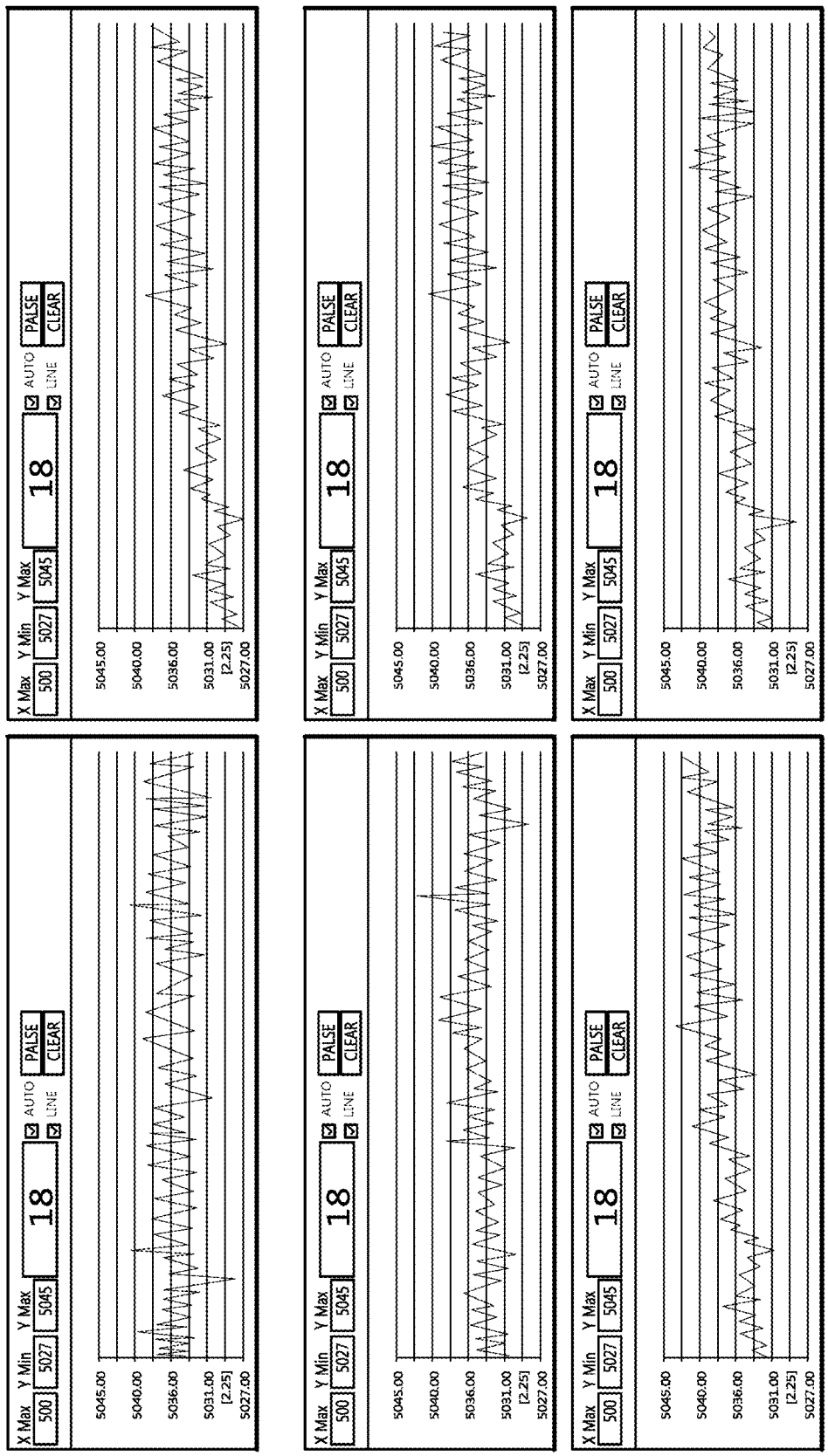

FIGS. 12A, 12B and 12C illustrate an example of analyzing whether an attitude of a user is changed in the monitoring server illustrated in FIG. 10.

FIG. 12A illustrates the sensing values received by six sensor modules when the user does not move in the mattress. Referring to FIG. 12A, it can be seen that the sensing values received by six sensor modules periodically fluctuate according to the breathing of the user.

FIG. 12B illustrates the sensing values received by six sensor modules when the user turns over. Referring to FIG. 12B, it can be seen that the sensing values received by six sensor modules periodically fluctuate to a predetermined value or more.

FIG. 12C illustrates the sensing values received by six sensor modules when the user turns over. Referring to FIG. 12C, since a turn-over state is not stable, noise is detected in the sensing value. However, when the state is stabilized, the sensing value may periodically fluctuate according to the breathing of the user.

Referring back to FIG. 10, the monitoring server 1020 may provide state monitoring result information to the user terminal 1030. The user terminal 1030 may include a PC, a mobile terminal, a tablet PC, or a laptop PC.

In an embodiment, the monitoring server 1020 may provide the state monitoring result information to the user terminal 1030 according to a request from the user terminal 1030. Alternatively, the monitoring server 1020 may provide a push message including the state monitoring result information to the user terminal 1030. The user terminal 1030 displays the received state monitoring result information on a screen.

The monitoring server 1020 may provide the state monitoring result information to the medical team terminal 1040 or a medical institution server. The medical team terminal 1040 may include a terminal owned by a medical team or a terminal provided in a medical institution and may include the PC, the mobile terminal, the tablet PC, or the laptop PC.

Figure 13:
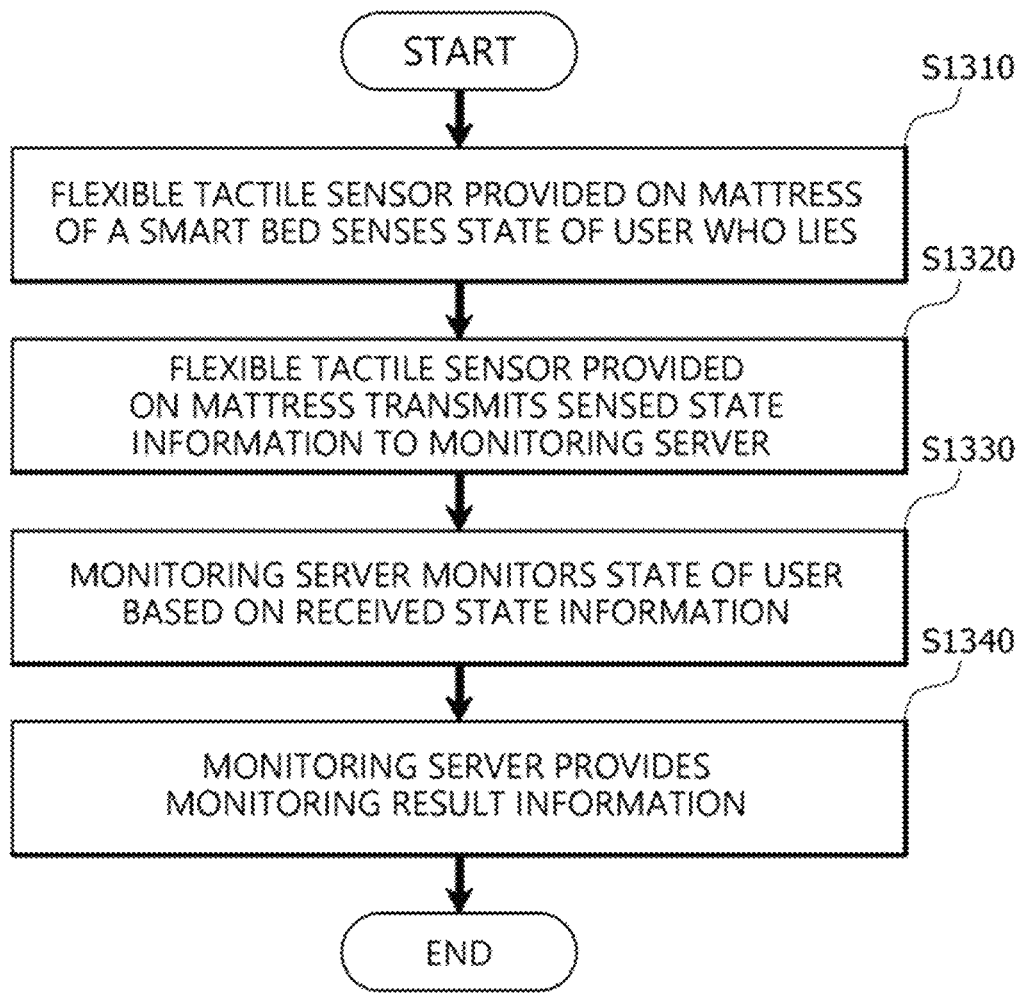
FIG. 13 is a flowchart for describing a user state monitoring method performed by the user state monitoring system illustrated in FIG. 10.

FIG. 13 is a flowchart for describing a user state monitoring method performed by the user state monitoring system illustrated in FIG. 10.

Referring to FIG. 13, the flexible tactile sensor included in the mattress of the smart bed 1010 senses the state of the user who lies (step S1310).

The flexible tactile sensor is positioned at a point corresponding to a specific portion of the user who lies on the mattress to sense the state of the user. For example, the flexible tactile sensor is positioned below or directly below a specific portion (e.g., chest) of the user. The flexible tactile sensor may be positioned to overlap a specific portion (e.g., chest) of the user in the direction of the thickness of the mattress. At least one flexible tactile sensor may be positioned on the mattress.

The flexible tactile sensor includes a sensor array constituted by the tactile sensor module and a communication unit. The tactile sensor module may have a structure described in FIGS. 3 to 8.

The flexible tactile sensor provided in the mattress transmits the sensed state information to the monitoring server (step S1320).

When the state information is received from the flexible tactile sensor of the smart bed 1010, the monitoring server 1020 analyzes and monitors the state of the user based on the received state information (step S1330). For example, the monitoring server 1020 may analyze and monitor the breathing state of the user based on the movement state information of the chest, which is received by the flexible tactile sensor of the smart bed.

The monitoring server 1020 may provide the monitoring result information to the user terminal, the medical team terminal 1040, or the medical institution server (S1340).

The user terminal 1030 or the medical team terminal 1040 displays the received state monitoring result information on the screen. The present invention has been described with reference to the preferred embodiments, but those skilled in the art will understand that the present invention can be variously modified and changed without departing from the spirit and the scope of the present invention which are defined in the appended claims.

INDUSTRIAL APPLICABILITY

The present invention relates to a smart bed, and a user state monitoring system and a user state monitoring method using the same, and more particularly, to a smart bed that can accurately detect a state of a user and monitoring the state of the user by using a flexible tactile sensor, and a user state monitoring system and a user state monitoring method using the same.

What is claimed is:
1. A smart bed comprising an array of tactile sensors configured to sense a state of a user lying on the mattress,
   Wherein each tactile sensor in the array of the tactile sensors comprises:
   a polymer layer,
   a first metal layer formed over the polymer layer,
   a first sensor layer including a first strain gauge formed over the first metal layer and a first metal wire connected to the first strain gauge, the first strain gauge being configured to change resistance depending on a first strain,
   a first cover layer configured to protect the first sensor layer,
   a second metal layer formed under the polymer layer,
   a second sensor layer including a second strain gauge formed under the bottom of the second metal layer and a second metal wire connected to the second strain gauge, the second strain gauge being configured to change resistance depending on a second strain, and a second cover layer configured to protect the second sensor layer.

2. The smart bed of claim 1, wherein the array of tactile sensors are embedded in a mattress body.

3. The smart bed of claim 1, wherein the array of tactile sensors include a detachment/attachment portion on one surface thereof, and are configured to be detached from/attached to a mattress body using the detachment/attachment portion.

4. The smart bed of claim 1, wherein the array of tactile sensors are configured to be positioned below and across a chest of the user.

5. A system for monitoring a state of a user, the system comprising:

a smart bed comprising a mattress, wherein the mattress comprises an array of tactile sensors configured to sense a state of a user lying on the mattress, wherein the smart bed is configured to transmit a state information representing the sensed state; and a server comprising at least one processor and at least one communication interface, wherein the at least one communication interface is configured to receive the state information from the smart bed and wherein the at least one processor is configured to monitor the state of the user based on the received state information, wherein each tactile sensor in the array of the tactile sensors comprises:

a polymer layer, a first metal layer formed over the polymer layer, a first sensor layer including a first strain gauge formed over the first metal layer and a first metal wire connected to the first strain gauge, the first strain gauge being configured to change resistance depending on a first strain, a first cover layer configured to protect the first sensor layer, a second metal layer formed under the polymer layer, a second sensor layer including a second strain gauge formed under the bottom of the second metal layer and a second metal wire connected to the second strain gauge, the second strain gauge being configured to change resistance depending on a second strain, and a second cover layer configured to protect the second sensor layer.

6. The system of claim 5, wherein the array of tactile sensors are configured to be positioned below and across a chest of the user.

7. The system of claim 6, wherein the array of tactile sensors are configured to sense a movement state of the chest of the user, and wherein the at least one processor of the server is configured to monitor a breathing state of the user based on the movement state of the chest of the user.

* * * * *